United States Patent [19]

Linder et al.

[11] 4,389,373
[45] Jun. 21, 1983

[54] HEATED ION CURRENT SENSOR FOR HIGH TEMPERATURES

[75] Inventors: Ernst Linder, Mühlacker; Klaus Müller, Tamm; Helmut Maurer, Schwieberdingen, all of Fed. Rep. of Germany

[73] Assignee: Robert Bosch GmbH, Stuttgart, Fed. Rep. of Germany

[21] Appl. No.: 214,718

[22] Filed: Dec. 9, 1980

[30] Foreign Application Priority Data

Feb. 16, 1980 [DE] Fed. Rep. of Germany ....... 3005928

[51] Int. Cl.³ ............................................. G01N 27/12
[52] U.S. Cl. ..................................... 422/98; 324/465
[58] Field of Search ................................. 422/94–98, 422/90; 324/465; 338/22 SD, 31; 204/195 S

[56] References Cited

U.S. PATENT DOCUMENTS

| 3,999,947 | 12/1976 | Mihara et al. | 422/98 |
| 4,033,169 | 7/1977 | Fujishiro et al. | 422/90 |
| 4,164,539 | 8/1979 | Johnston | 422/96 |
| 4,193,965 | 3/1980 | Cullingford et al. | 73/27 R |
| 4,197,089 | 4/1980 | Willis et al. | 422/98 |
| 4,223,550 | 9/1980 | Takahama et al. | 422/98 |
| 4,241,019 | 12/1980 | Nakatani et al. | 422/98 |

Primary Examiner—Michael S. Marcus
Attorney, Agent, or Firm—Frishauf, Holtz, Goodman & Woodward

[57] ABSTRACT

To guide gas to the electrode of a high temperature sensor, a substrate (1), for example of ceramic or ceramic-coated metal has electrodes (3, 4; 7, 8; 16, 17) applied thereto, for example in meander pattern, spaced from each other. A heater is applied to the substrate, either on the same side (FIGS. 2, 3) or on the backside (FIG. 1). Gas is guided to the electrodes by projecting ridges and posts (11, 12) to thereby prevent fouling of the electrodes by gas; the ridges and posts, additionally, can be protected by a cover (18) FIG. 3, thereover. The spacing 13 between the ridges and posts, and the cover, if provided, is so arranged that resonance chambers are formed which are resonant at the expected frequencies of, for example, engine knocking or unusual combustion conditions. Guiding the gas by the ridges and posts permits differential effects to be obtained by, selectively, polarizing the electrode to have the negative or positive electrode, respectively, adjacent the gas inlet to provide repulsion, or attraction effects on the gas, and thereby obtain either a differential pressure sensor, or sensor of maximum sensitivity.

10 Claims, 3 Drawing Figures

HEATED ION CURRENT SENSOR FOR HIGH TEMPERATURES

The invention is based on a sensor for detecting ion currents suitable for use at high temperatures, e.g. to determine ion currents in combustion chambers of furnaces, engines or the like.

BACKGROUND

U.S. Pat. No. 3,999,947 describes a sensor having two electrodes and a heater element on a carrier for measuring hydrocarbon mixtures. The electrodes are disposed at a great distance from one another and are covered with a gas-sensitive element which splits the hydrocarbon material into ions and electrons. The gas-sensitive layer is difficult to manufacture and can be used only in the low temperature region. At high temperatures, chemical processes take place in the gas-sensitive layer which tend to destroy the layer and gum up the electrodes. Thus, such sensors cannot be used at high temperatures.

THE INVENTION

It is an object to provide at high temperature sensor providing suitable output currents representative of ionizable hydrocarbon gases, occurring, for example, in the combustion chamber of an internal combustion (IC) engine, a furnace or the like; and which, additionally, can be used to determine knocking of an IC engine.

Briefly, a substrate with an insulating surface, such as a ceramic or a plate of steel or aluminum coated with an insulator has applied at one side two electrodes, spaced from each other, and forming a measuring region. The plate is essentially rectangular, and thus defines a major, or longitudinal axis, and a minor, or transverse axis. A heater is located on the same side, or on the other side of the plate to heat the measuring region to a high temperature, preferably to a temperature in excess to that of the gases. In accordance with the invention, and to direct gas to the electrodes and prevent fouling thereof, projections such as ridges, upstanding posts or the like are formed on the substrate leading the gas towards the electrodes. The ridges, and the space over the electrodes can be covered by a cover plate. The spacing between the ribs, and the cover plate, if provided, preferably can be dimensioned to form a resonance chamber having resonance at frequencies expected to occur during detonation or engine knocking, or, generally, to specific frequencies expected within the combustion chamber.

In accordance with a feature of the invention, the heating conductor and the measuring electrodes are located on the same side of the insulating carrier plate. In this way, both layers can be applied simultaneously, i.e. the carrier does not have to be turned around and fabricated on both the front and the back side. The most desirable method of manufacture was found to be vapor deposition or printing of the heating conductor and the measuring electrodes. In special applications, it has also been found to be desirable to dispose measuring electrodes on both sides of the carrier. In this way, one obtains two sensors one of which may be used as a reference sensor or the two sensors may have different sensitivities so as to enlarge the measuring region. In order to obtain special measuring effects, a system of channels consisting of ridges and ridges or continuous ridges on one or both sides of the measuring electrodes can be used. Such an arrangement can alter the sensitivity of the measuring electrodes or may result in improved detection of hydrocarbon materials which occur in pressure waves, for example during engine knocking of an internal combustion (IC) engine. This effect can be enhanced by covering the ridges or supports with a cover plate. If the gas flow is expected from a particular direction, it is desirable to increase the sensitivity of the sensor by arranging the ridges or supports asymmetrically with respect to the electrodes. For applications in flowing gas, the polarity of the voltage of the measuring electrode facing the flow is important to obtain special effects. If a positive voltage is applied to this measuring electrode, ionized gas of negative polarity is attracted by the electrode and results in an increase of sensitivity. If the negative electrode first meets the ionized gas of negative polarity, the result is repulsion which is overcome, however, by pressure fluctuations triggered, for example by the detonations consequent upon knocking of an internal combustion engine so that one obtains a pressure-sensitive sensor for the ion current.

DRAWING

DESCRIPTION OF THE INVENTION

Figure 1:
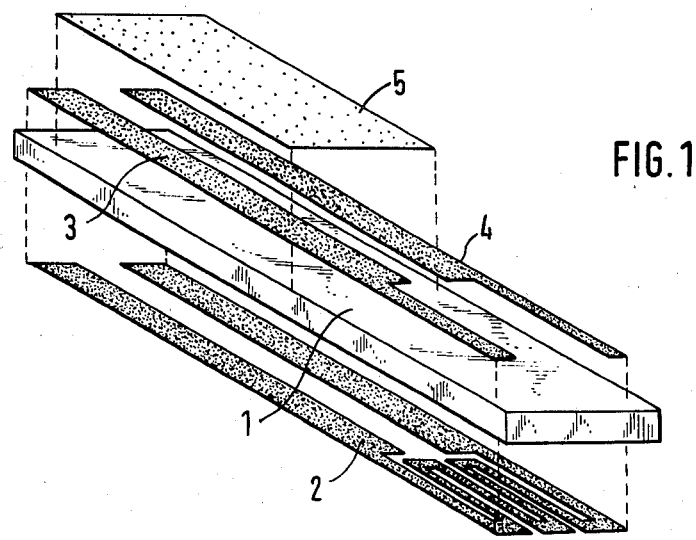
FIG. 1 is a phantom-perspective view illustrating a basic structure of the sensor suitable to explain the operation thereof.

The sensor illustrated in FIG. 1 includes a rectangular carrier plate 1, consisting of temperature-resistant material. A suitable material is, for example a, ceramic. However, it is desirable to use materials with good heat conductivity, for example aluminum or steel, but in that case it is necessary to use an additional insulating layer, for example aluminum oxide which may be applied, for example, by a plasma spraying process or a silk screening process. Rolled on the bottom side of the carrier plate 1 is a conductor track 2 which forms meandering loops in the region of the electrodes and serves for heating the plate 1. Disposed on the top surface of the carrier plate 1 are two electrodes 3 and 4 serving as measuring electrodes. The measuring voltage is applied to these electrodes. In principle, any electrical conductor may be used as material for the electrodes or the conductor track. However for measurements at high temperatures, it is recommended to use noble metals, for example platinum, gold or palladium. The electrodes 3 and 4 and the conductor track 2 are printed, rolled on or vapor deposited. Consequently they will be in form of layers. In the region they are not exposed to gas, the electrodes 3 and 4 can be covered with an insulating layer 5.

At high temperatures, hydrocarbon substances already occur in the ionized state. Therefore, if the sensor is introduced into the combustion chamber of a gas or oil heater or into the combustion chamber of an internal combustion engine, the ionized gas releases an ion current between electrodes 3 and 4 which is dependent on the quantity of the ionized gas which is present. It is then possible to pick off a voltage from a measuring resistor placed in the current circuit whose magnitude is proportional to the strength of the ion current and hence to the ionized gas. The ion current and its time behavior thus permit conclusions regarding the kind of combustion of the fuel-air mixture. It is also possible to determine whether the combustion taking place is intensive and rapid or extended in time.

The effect of heating the ion current sensor is that the electrodes can not become coated with soot because any soot is immediately burned away by the heat of the heater. Furthermore the electrodes 3 and 4 are temperature stabilized, i.e. a measuring error due to temperature fluctuations in the medium to be measured can not take place. The heater heats the sensor in such a way that the gas temperature can never reach the sensor temperature. In the combustion chamber of internal combustion engines, this temperature can be as high as 1000° C. at the point of measurement. Another effect is that the gas in the vicinity of the measuring point does not cool off, which would result in measurment errors.

Figure 2:
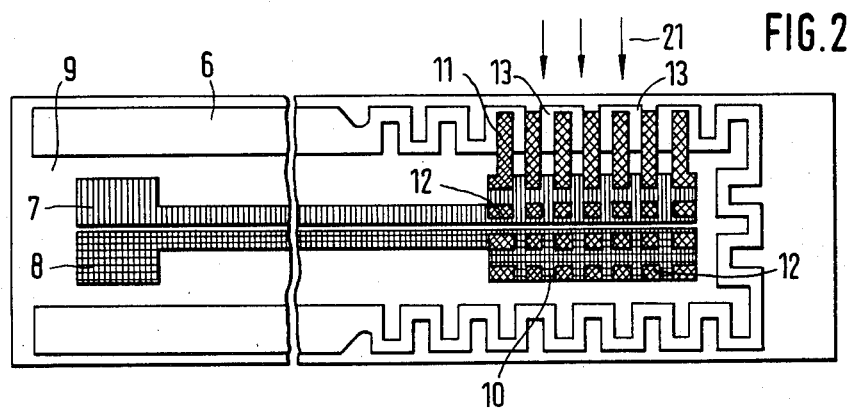
FIG. 2 is a top view of the sensor incorporating the structure of the present invention.

Embodiment of FIG. 2: the heater conductor 6 and the electrodes 7 and 8 are applied to the same side of the carrier plate 9. In the measuring region 10, the heater conductor 6 is again formed in a meandering pattern. In order to prevent the electric field of the heater from affecting the measuring electrodes 7 and 8, the heater conductor 6 is suitably covered in the electrodes measuring region 10 by an insulating layer not shown in the drawing. Ridges 11 are disposed in the measuring region 10. They are located asymmetrically with respect to the gas flow direction; these ridges serve to guide the gas toward the electrodes i.e. in a direction of the minor axis of the plate, from the longitudinal side inwardly.

Supports 12 in the form of stubs or posts are located in the region of the electrodes. are disposed supports 12. The ribs 11 which can also be continuous and the supports 12 are also vapor deposited or printed on the carrier plate 9. For example heights of 30-50μ have been found to be sufficient. The gas 21 to be measured then flows through the channels 13 formed in this manner. The channels 13 may have a width of, for example, 0.2-1 mm.

The final determination of the channel dimensions takes place from the viewpoint of manufacturing possibilities and the sensitivity of the sensor. If an analysis of the ion current behavior is needed to determine the degree of quiescence of combustion or to determine knocking of an internal combustion engine, it is possible to form the channels in such a way that they act like a resonant body. In that case, the length of the channels is extended to or limited to a quarter or an uneven multiple of the wavelength of the frequency to be measured. The resonating volume then defines a Helmholtz space resonator. If the sensor is to be used for example for measuring knocking in an internal combustion engine, the resonator should be tuned approximately to a region from 5-10 kH, because as is well known, knocking or spurious detonation takes place in this region, the exact frequency depending on the type of internal combustion engine. In this way, the ion current generated by the gas 21 is increased if the gas 21 is exposed to pressure fluctuations in the resonance region.

The disposition of the ridges 11 can serve to obtain another effect however. If the flowing gas 21 must overcome a certain resistance in the channels, then the width of the channels 13 may be used to change the sensitivity of the measuring electrodes 7, 8. Narrow channels 13 and wide bridges 11 reduce the sensitivity of the measuring electrodes 6, 7.

By choosing the polarity of the electrodes with respect to the flowing gas 21, the sensor may be optimized for various applications. For example, if the sensor is to be made sensitive to ionized gas occurring the pressure fluctuations, it is recommended to apply the negative voltage to the electrode 7. Ionized gas of negative polarity is then repulsed by the electrode 7 and can not enter the neck of the channel. However, if the amplitude of the pressure fluctuations is large enough, the gas 21 enters the channels 13 and reaches the field between the electrodes 7 and 8 which causes ion current fluctuations. A sensor constructed in this way is especially suitable for measurements of engine knocking. The opposite effect is obtained if the electrode 7 is charged positively. In that case, the negatively ionized gas is attracted by the positive electrode and thus can enter the channels more easily to release an ion current at the electrodes. The sensor is then more sensitive.

If the rear surface of the carrier plate 9 also carries a pair of electrodes, combination measurements are possible. For example one of the pairs of electrodes may be used to measure the ion current behavior in an ionized gas while the other electrode pair responds only to knocking. Alternatively the sensitivity of the two electrode pairs with respect to one another may be so adjusted as to obtain as large a measuring region as possible. If the gas is highly ionized, resulting in high ion currents, it is possible to overload the electrode 7, 8 so that the indication is no longer linear with increasing or decreasing ion components. If channels 13 are disposed on one of the electrode sides to cause a resistance to diffusion, these channels represent a preliminary resistance to the flow of the gas 21, which reduces the ion current to the electrodes and makes the electrodes on one side less sensitive.

Figure 3:
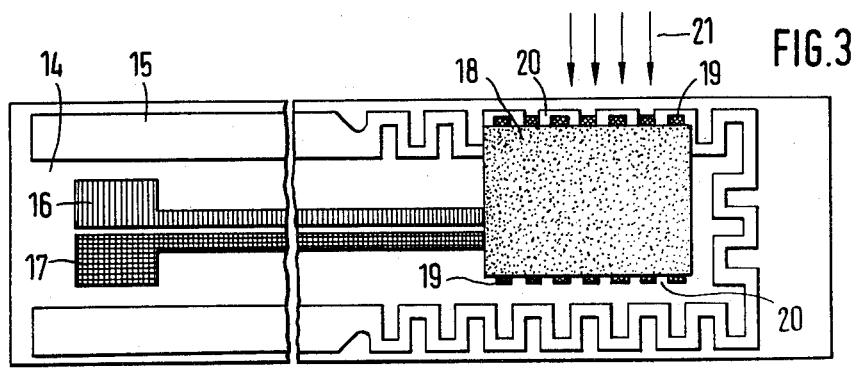
FIG. 3 is a top view of the sensor illustrating another embodiment.

Embodiment of FIG. 3: a heater conductor 15 is applied to a carrier plate 14 and forms a meandering pattern in the measuring region of the electrodes. Electrodes 16 and 17 are disposed in the middle of the plate 14 The measuring region is covered by a plate 18 resting on continuous ridges 19. The ridges 19 and the plate 18 are arranged asymmetrically with respect to the electrodes 16 and 17, so that the flowing gas 21 is already channeled in the channels 20 when it reaches the electrodes 16 and 17.

The plate 18 has the purpose of protecting the electrodes 16, 17 and the ridges 19 or the supports from being damaged by gross contaminations of the gas as well as to increase the resonator effect which may be desired for example for knocking measurements. In other respects, the sensor shown in FIG. 3 is similar to the sensor of FIG. 2 and operates similarly.

We claim:
1. Sensor for detecting ion currents in mixtures of hydrocarbon substances comprising
an essentially rectangular substrate plate (1) having a major axis and a minor axis, said plate having an insulated surface;
two layer-like electrodes (3, 4; 7, 8; 16, 17) located on one major surface of the substrate plate inwardly of marginal regions of the substrate plate, along the major axis, spaced from each other, and having a measuring region on a portion thereof;
a heater (2, 6, 15) located adjacent the electrodes to heat at least the measuring region;
and gas flow guide means (11, 12; 18) comprising ridges projecting from the major surface of the substrate and leading from a marginal region thereof in the direction along the minor axis towards the measuring region of the electrodes to guide gas, the ionization of which is to be measured, to the measuring region of said electrodes.

2. Sensor according to claim 1 further including projecting posts or stubs projecting from the said one side surface of the substrate plate.

3. Sensor according to claim 1 wherein said gas flow guide means, further comprises a cover plate (18) positioned over and covering said ridges.

4. Sensor according to claim 1 wherein said ridges are located asymmetrically on said substrate plate with respect to said electrodes.

5. Sensor according to claim 1 wherein the ridges (11) are spaced from each other by a predetermined distance (13) to form resonance spaces between the ribs.

6. Engine knock sensor comprising
the sensor of claim 1
wherein the ridges, are spaced from each other by a predetermined distance (13) and form resonance chambers therebetween, dimensioned to resonate at expected engine knocking frequency.

7. Engine knock sensor according to claim 6 further comprises a cover (18) placed over said ridges, the cover, and the space between said ridges forming, in combination, resonance tubes or duct-like chambers dimensioned to resonate at expected engine knocking frequency.

8. Sensor according to claim 1 wherein two sets of measuring electrodes are provided, one set of measuring electrodes is disposed on one side of the plate-like substrate and another set of measuring electrodes is disposed on the other side of the substrate; and ridges (16) forming gas flow guiding means extend from the substrate leading towards the sensing region of the sets of electrodes are formed on both sides of the substrate to guide gas to be measured to both sets of electrodes.

9. Sensor according to claim 8 wherein the sets of electrodes have different response sensitivity.

10. Sensor according to claim 9 wherein the ridges at one side of the sensor and associated with one set of electrodes define gas flow directing channels for ducts or tubes dimensioned to resonate at expected disturbance frequencies;

and the set of electrodes at the other side of the substrate is exposed to ambient gas.

* * * * *

UNITED STATES PATENT AND TRADEMARK OFFICE
CERTIFICATE OF CORRECTION

PATENT NO. : 4,389,373
DATED : June 21, 1983
INVENTOR(S) : Ernst LINDER et al

It is certified that error appears in the above—identified patent and that said Letters Patent is hereby corrected as shown below:

Claim 10, col 6, li 16, "according to claim 9" to be -- according to claim 8 --.

Specification:

Col 3, line 32 delete phrase ...are disposed supports 12

Col 4, lines 39 & 45 the word "ridges" in all three instances, should be -- ribs --.

Signed and Sealed this

Eleventh Day of October 1983

|SEAL|

Attest:

Attesting Officer

GERALD J. MOSSINGHOFF

Commissioner of Patents and Trademarks